(12) United States Patent
Kristiansen (10) Patent No.: US 6,537,223 B1
(45) Date of Patent: Mar. 25, 2003

(54) PROBE HEAD

(75) Inventor: Knut Kristiansen, Horten (NO)

(73) Assignee: Medi-Stim AS (NO)

( * ) Notice: Subject to any disclaimer, the term of this patent is extended or adjusted under 35 U.S.C. 154(b) by 0 days.

(21) Appl. No.: 09/654,921

(22) Filed: Sep. 5, 2000

(51) Int. Cl.$^7$ ................................................ A61B 8/14
(52) U.S. Cl. ...................................... 600/459; 600/468
(58) Field of Search ................................ 600/437, 441, 600/443, 453–457, 459–468; 385/7

(56) References Cited

U.S. PATENT DOCUMENTS

| | | | |
|---|---|---|---|
| 4,227,407 A | | 10/1980 | Drost |
| 4,770,185 A | * | 9/1988 | Silverstein et al. ......... 600/454 |
| 5,284,148 A | * | 2/1994 | Dias et al. .................. 600/454 |
| 5,588,436 A | * | 12/1996 | Narayanan et al. ......... 600/459 |

OTHER PUBLICATIONS

K. Saatvedt, M.D. et al., *Flowmetry During Minimally Invasive Coronary Surgery (MICS)*, Medi–Stim Clinical Cases, vol. 3, No. 1, Sep. 1996, pp. 4.

K. Saatvedt, M.D. et al., *The Importance of Intraoperative Flow Measurements During MIDCAB Procedures*, Medi–Stim Clinical Cases, vol. 3, No. 2, Nov. 1996, pp. 4.

J. van der Meulen, M.D. et al., *Detection of a Twisted Saphenous Vein Graft During Coronary Artery Bypass Surgery*, Medi–Stim Clinical Cases, vol. 4, No. 1, Jan. 1997, pp. 4.

B. Cherrier et al., *Reduced Flow in the Right Internal Mammary Artery (RIMA) Due to Insufficient Graft Length*, Medi–Stim Clinical Cases, vol. 4, No. 2, May 1997, pp. 4.

G. Plate, M.D., Ph.D et al., *Detection of a Twisted Saphenous Vein Graft During Femoropopliteal Bypass*, Medi–Stim Clinical Cases, vol. 4, No. 3, Sep. 1997, pp. 4.

Prof. Einar Stranden, Ph.D., et al, *The Benefit of Flowmetry in Peripheral Vascular Surgery*, Medi–Stim Clinical Cases, vol. 4, No. 4, Sep. 1997, pp. 4.

H.L. Jakobsen, M.D. et al., *Detection of Flow Stop in Bypass Grafts during CABG*, Medi–Stim Clinical Cases, vol. 5, No. 1, Sep. 1998, pp. 4.

(List continued on next page.)

*Primary Examiner*—Marvin M. Lateef
*Assistant Examiner*—Ali M. Imam
(74) *Attorney, Agent, or Firm*—Knobbe, Martens, Olson & Bear, LLP (57) ABSTRACT

A one piece, sealed ultrasound probe head for measuring volume flow in vessels, which comprises a conventional ultrasound reflector (20) and piezo-electric crystals (23), mounted on a support element (30) which is permanently inserted into a housing (10) which is made of a resilient material and having gel spill guards (11) for limiting acoustic coupling gel spillage; and vessel retainer flaps (12) for retaining the vessel in a stationary position in the probe head. The probe head contains a supporting channel (16) capable of receiving and retaining on its surfaces an acoustic coupling gel. The resilient vessel retainer flaps (12) are capable of being flexed in order to selectively receiving or releasing the vessel into or out of the channel (16), and securing the vessel in a stationary position in said channel in order to allow flow measurement. The probe head in accordance with the invention may be used with any known probe device, including endoscopic probe devices.

23 Claims, 6 Drawing Sheets

OTHER PUBLICATIONS

Anders Lundell, M.D., Ph.D., *The prediction of femoropopliteo/crural bypass patency through transit–time flowmetry*, Medi–Stim Clinical Cases, vol. 6, No. 1, Jul. 1999, pp. 4.

Thomas Matzsch, M.D., Assoc Prof., *Transit–Time Flowmetry as Completion Control in Carotid Surgery*, Medi–Stim Clinical Cases, vol. 6, No. 2, Dec. 1999, pp. 5.

*The Accurate Tool for Quantitative Graft Patency Verification*, Medi–Stim, pp. 4

*Creating Hemodynamic Confidence . . . The CardioMed Flowmeter*, Med–Stim, 1995, pp. 4.

*Would You Trust Your Fingertip To Measure 49.8 ml/min?*, Medi–Stim, 1997, pp. 4.

*Medi–Stim InLine And ClampOn Flow Probesd*, Medi–Stim, 1997, pp. 2.

*Medi–Stim PeriVascular Transit Time Flow Probes*, Medi–Stim, 2000, pp. 2.

"Transonic V–Series Probes, Innovative Tools to Measure Flow in Microvessels Acute Studies", Nov. 1999; http://www.transonic.com/v–series probes.html.

"Transit Time Ultrasound Technology, Accurate, Direct, Continuous—The Gold Standard", Mar. 1999; http://www.transonic.com/transit time theory.html.

"Perivasular Flowprobes from A–Z", Transonic Systems Inc., Nov. 1995; http://www.transonic.com/peripro.pdf.

N. Nakayama et al., "Intraoperative Measurement of Arterial Blood Flow Using a Transit Time Flowmeter: Monitoring of Hemodynamic Changes During Cerebrovascular Surgery", *Acta Neurochir (Wien)*, (2001) vol. 143: pp. 17–24.

\* cited by examiner

PROBE HEAD

CROSS-REFERENCE TO RELATED APPLICATIONS

Not Applicable

BACKGROUND OF THE INVENTION

1. Field of the Invention

This invention relates to the field of probes. More specifically, the invention relates to an ultrasonic probe head for measuring volume flow in vessels, particularly blood flow in arteries and veins, and the use of such probe head during conventional and endoscopic surgery.

2. Description of Related Art

Ultrasound probes are used in several applications, one application being the measurement of volume flow in vessels in connection with surgery. Prior art probe heads for measuring volume flow in vessels (e.g. veins and arteries) are generally based on the fact that the time required for ultrasound to pass through the vessel fluid is slightly longer when the ultrasound is transmitted against the fluid flow, than when it is transmitted in the same direction as the flow. In order to generate such transmission and record the difference in transit time, prior art probe heads for measuring volume flow in vessels in general and in principle comprise two crystals for transmitting and receiving ultrasound waves, and a passive device for reflecting same. The crystals are disposed on the one side of the vessel, at equal but opposite angles with respect to a plane perpendicular to the vessel longitudinal axis. The reflecting device is disposed on the other side of the vessel, diametrically opposite the crystals. The crystals and the reflector are arranged such that ultrasound waves reciprocally travel from one crystal, through the vessel, being reflected off the reflector, and returning through the vessel to be received by the other crystal. In order to having the ultrasound waves travelling in an as homogenous medium as possible, the gaps between the vessel and the crystals and between the vessel and the reflector, are filled with an acoustic transmitting fluid, such as e.g. blood or water or—if the vessel is not otherwise immersed—an acoustic coupling gel.

In order to keep the vessel in a fixed and stationary position between the crystals and the reflector during measurement, prior art probe heads are equipped with a sliding device, which is opened to receive or release the vessel and closed to retain the vessel.

It is in e.g. surgical procedures, essential that the vessel remains in a stationary and fixed position within the probe head. It is also important that the gel is kept in place between the vessel and the probe head in order to ensure reliable measurement.

One problem with known probe heads is that the gel is not well contained, and that flow measurements over extended periods of time thus are compromised due to the influence of air or other fluids having different acoustic properties.

Known probe heads are also cumbersome to operate, in that they require the actuation of movable sliding devices in order to place the exposed artery or vein in the probe head. This can at best be difficult to accomplish, given the environment in which the probe heads are being used, and the small size of the probe heads.

Conventional probe heads must also to some extent be disassembled for cleaning and sterilisation after use. This is time consuming and exposed the probe heads for excessive wear.

It is therefore a long felt need for a probe head intended for volume flow measurement in vessels, that is easy to manufacture, operate and clean, and that retains the gel for an extended period in order to maintain sufficient acoustic coupling.

The present invention solves that need, in that the probe head according to the invention contains few parts that are easily manufactured by conventional techniques and, when assembled, comprises one sealed unit with no movable parts. The invented probe head is thus easy to clean and sterilise, requiring no disassembly and reassembly. Furthermore, the vessel may easily be placed in the invented probe head, only by the user slightly twisting the probe head. The probe head in accordance with the invention also comprises a channel which in an improved manner retains the gel for an extended period, thereby ensuring sufficient acoustic coupling.

BRIEF SUMMARY OF THE INVENTION

These and other objects and features of the invention are provided by an ultrasound probe head for measuring volume flow in vessels. In broad terms, the probe head comprises a housing, a support element, reflector-, crystal- and circuit means, and associated wires and cable.

The ultrasound reflector, piezo-electric crystals and circuit board are mounted onto respective dedicated surfaces in the support element, in an arrangement generally known in the art and electrically connected through wires to a measurement apparatus.

Inclined surfaces to which the crystals are mounted, are disposed in the upper region of the support element, symmetrically about a support element vertical axis. The support element is furthermore equipped with a bore for passing the electrical cable and a slit and a wire compartment for housing the electrical wires.

The ultrasound reflector is attached to the support element by fastening means, while the crystals and circuit board are affixed to the support element by means of a resilient compound. The support element, with the above mentioned parts assembled to it, is sealably coated with a resilient compound.

The probe head housing is made of a resilient material and comprises a compartment into which the support element is placed, a cable bore for the electrical cable bundle containing the wires to the crystals and circuit board, a recess into which a portion of the reflector is passed, spill guards for limiting acoustic coupling gel spillage, and vessel retainer flaps for retaining the vessel in a stationary position in the probe head while measurements are being performed.

The assembled probe head housing and support element are further sealed to constitute one sealed probe head unit, by the application of a resilient compound in the upper region of the housing.

The resilient compound filled in the upper region of the housing, above the affixed crystals and circuit board, forms together with the vessel retainer flaps, part of the reflector and the gel spill guards, a channel with generally planar surfaces, capable of receiving, supporting and retaining the vessel and an acoustic coupling gel.

The resilient vessel retainer flaps are flexible in order to letting the vessel be slipped into the channel. The flaps secure the vessel in a stationary position in said channel, and are sufficiently flexible for allowing a selective release of the vessel from the channel.

The assembled probe head may be used in connection with conventional surgery, where arteries and veins are exposed, and may be fitted to any known probe type. The assembled probe head may also be used in endoscopic procedures and may be fitted to any known endoscopic probe type.

The gel spill guards upper region or edge may have either an arcuate (concave or convex) horizontal or inclined shape.

The probe head housing upper lateral edges are formed as inwardly directed flanges adapted to catch the support element upper region.

BRIEF DESCRIPTION OF THE DRAWINGS

FIG. 1 shows a probe head housing according to an embodiment of the present invention, in side view (FIG. 1a), front view (FIG. 1b) and top view (FIG. 1c).

FIG. 2 shows an ultrasound reflector according to an embodiment of the present invention, in bottom view (FIG. 2a), side view (FIG. 2b) and front view (FIG. 2c).

DETAILED DESCRIPTION OF THE INVENTION

Referring to FIGS. 1–6, the preferred embodiment of the ultrasound probe head of the present invention comprises a probe head housing (10), support element (30) and an ultrasound reflector, circuit board (24) and piezo-electric crystals (23).

Figure 2A:
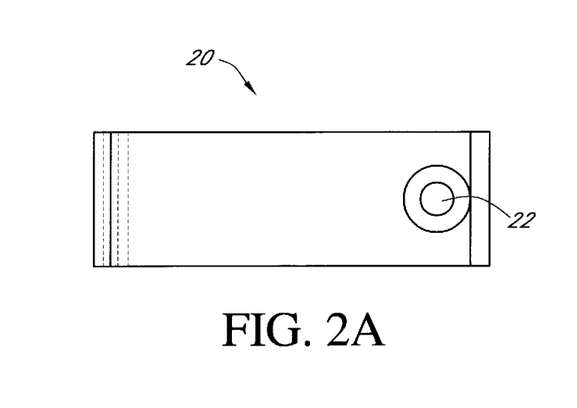
Figure 2B:
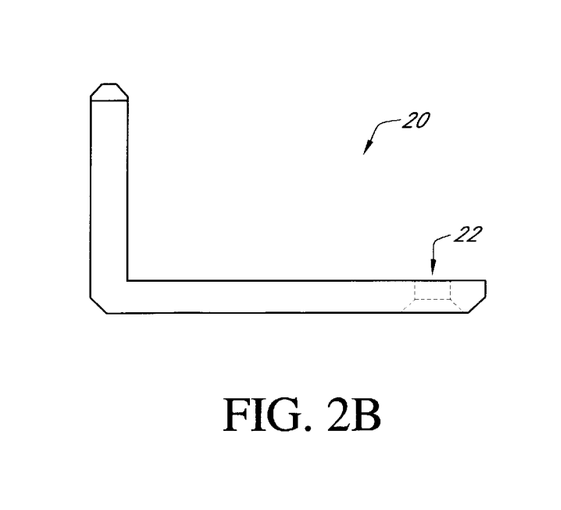
Figure 2C:
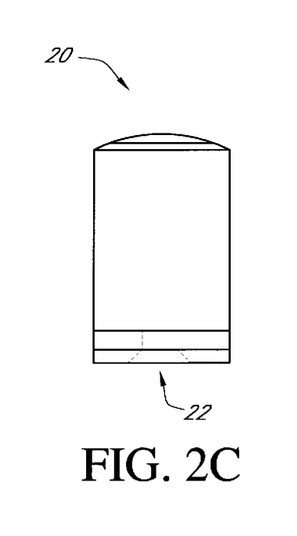
Figure 3:
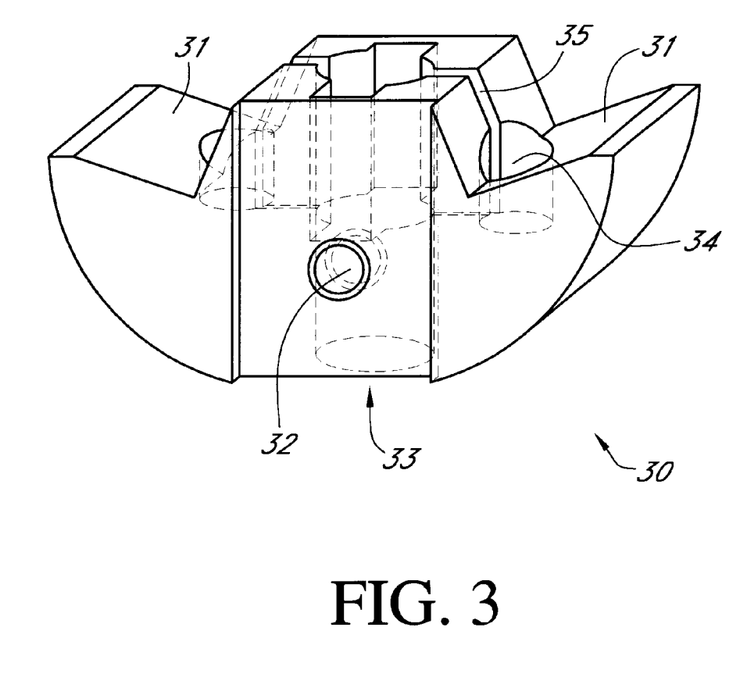
FIG. 3 shows a perspective rear view of a support element according to an embodiment of the present invention.
Figure 5:
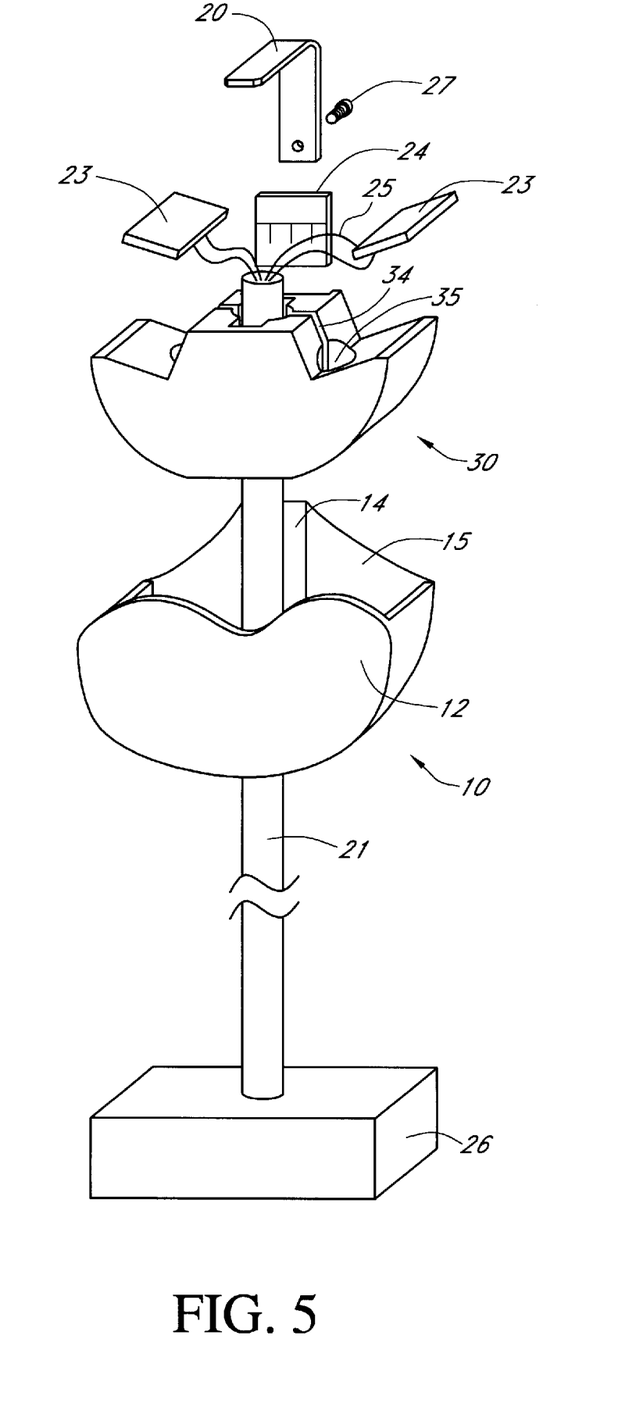
FIG. 5 shows a perspective exploded front view of a probe head according to an embodiment of the present invention.

The ultrasound reflector (20) is attached to the support element (30) by means of a fastening device, for instance a bolt or pin (27) through respective holes (22, 32).

The piezo-electric crystals (23) are electrically connected by wires (25) to a circuit board (24), all being electrically connected to a measurement apparatus (26) through an electrical cable (21).

The support element (30), supports the piezo-electric crystals (23) on respective inclined crystal supporting surfaces (31), disposed on its upper region thereof and symmetrically about a support element vertical axis, and to which said crystals (23) are affixed. The circuit board (24) is disposed in the space between the crystals. Referring to FIG. 3, the support element also comprises a bore (33) through which the electrical cable (21) is passed, a slit (34) and a compartment (35) for housing the electrical wires (25).

Figure 1A:
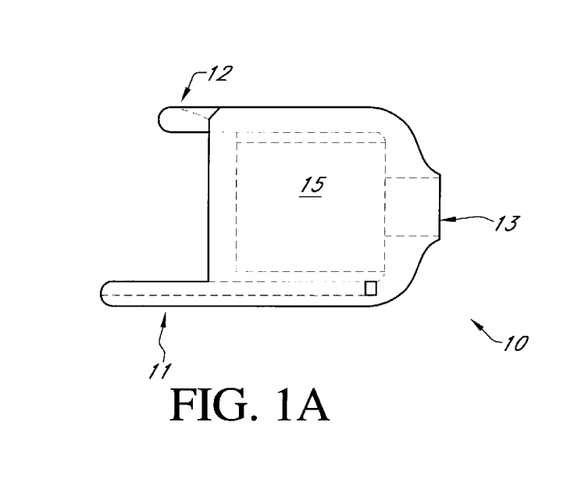
Figure 1B:
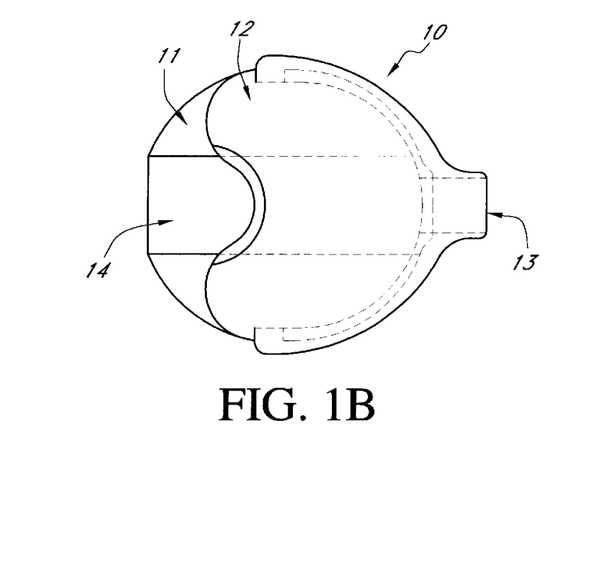
Figure 1C:
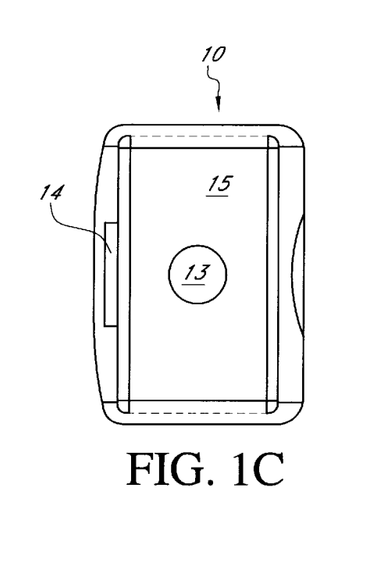
Figure 4:
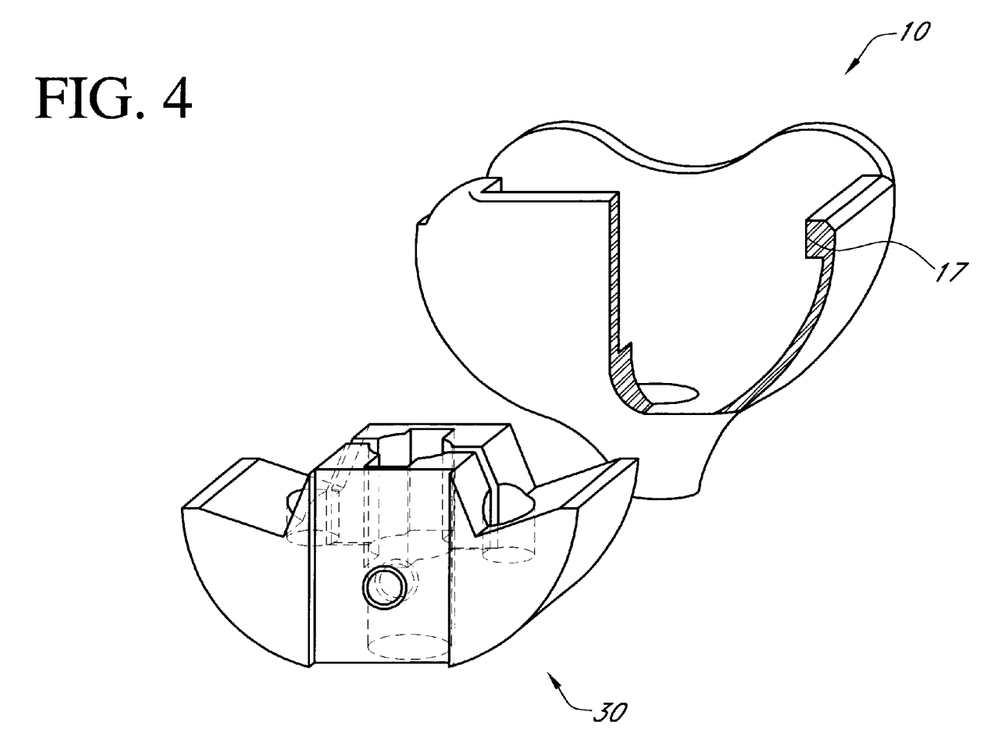
FIG. 4 shows a perspective rear view of a support element and, partly cut-away, a probe head housing, according to an embodiment of the present invention.

Referring to FIG. 1, the probe head housing (10) has a compartment (15) for receiving the support element (30), a cable bore (13) through which the electrical cable (21) from the support element is passed, and a recess (14) for receiving a portion of the reflector (20). In addition, referring to FIGS. 1, 5 and 6, the housing also comprises gel spill guards (11) for limiting spillage of acoustic coupling gel, and resilient vessel retainer flaps (12) for selectively admitting, retaining and releasing the vessel in a stationary position in the probe head. Referring to FIG. 4, The probe head housing upper lateral edges are formed as inwardly directed flanges (17) adapted to catch the support element upper region.

The probe head housing is made of a resilient material, preferably silicone, but may be selected from a group comprising silicone, plastics, rubbers, etc.

The reflector (20), said ultrasound crystals (23), and said circuit board (24) are fixedly attached to said support element (30) in a fashion generally known in the art, and the assembly thereof is sealably coated with a resilient compound, preferably silicone.

Figure 6:
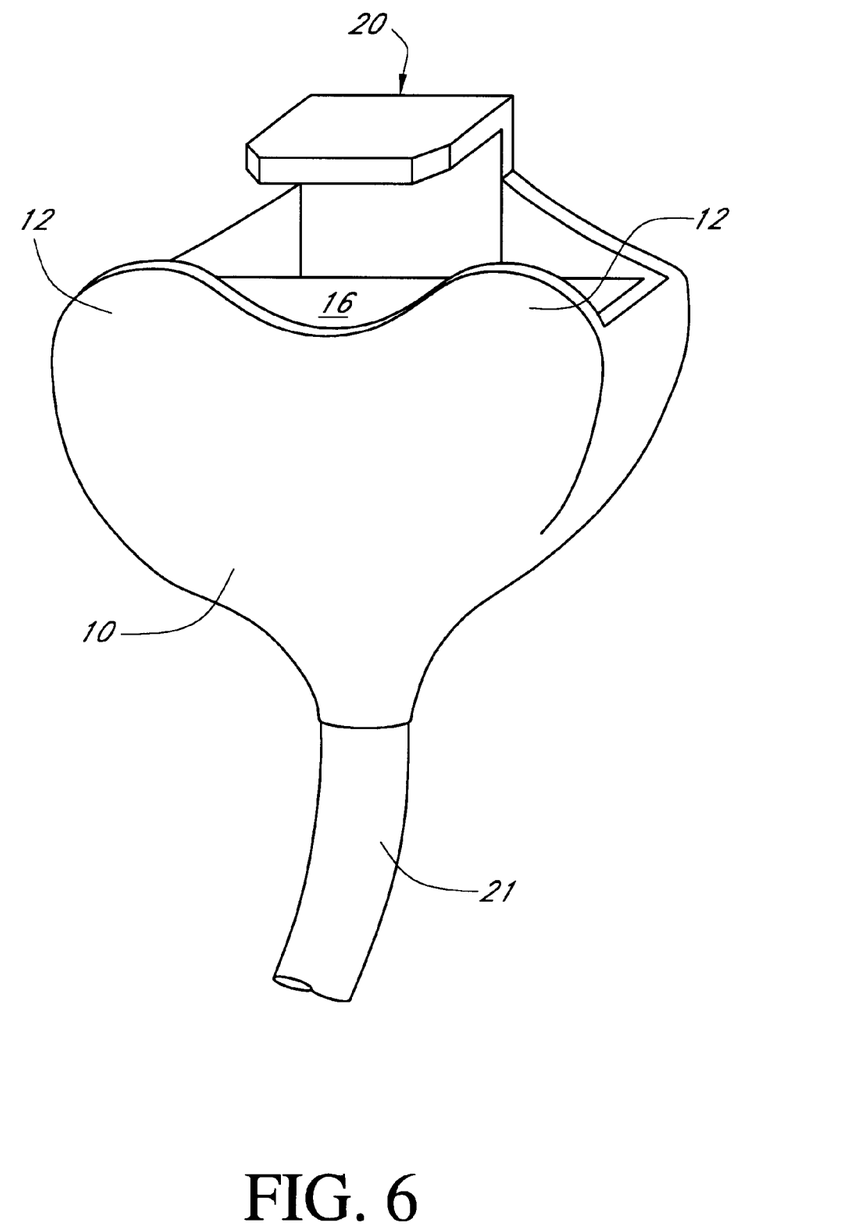
FIG. 6 shows a perspective front view of an assembled probe head according to an embodiment of the present invention.

The assembly comprising the probe head housing (10) and the assembled support element are further sealed to constitute one sealed probe head unit, by the application of a resilient compound, preferably silicone, in the upper region of the housing. This, in combination with the vessel retainer flaps (12), reflector (20) and gel spill guards (11), forms a vessel supporting channel (16) with generally planar surfaces which is capable of receiving and retaining on its surfaces an acoustic coupling gel. The above mentioned resilient compound in the preferred embodiment of the present invention is silicone, but may be selected from a group comprising silicone, plastics, rubbers, etc.

The resilient vessel retainer flaps (12) are capable of selectively being flexed in order to letting the vessel be slipped into the channel (16), and to selectively releasably securing the vessel in a stationary position in said channel in order to allow flow measurement, and selectively being flexed in order to releasing the vessel from the channel (16).

The assembled probe head in accordance with the preferred embodiment of the present invention may be used for measuring volume flow in blood vessels, either during conventional surgery where the blood vessels are exposed, or in endoscopic procedures where the vessels are accessed through holes in the thorax.

When using the probe head, the user first coats the probe head in acoustic coupling gel, which then is contained within the channel (16). The user then slips the vessel into the channel containing gel, by slightly flexing the retainer flaps (12) and/or the vessel. The vessel is retained in contact with the gel inside the channel for the desired duration, after which the reverse operation is performed to release the vessel from the channel.

The foregoing description and the embodiments of the present invention are to be construed as mere illustrations of the application of the principles of the invention. The foregoing is not intended to limit the scope of the claims, but the true spirit and scope of present invention is defined by the claims.

What is claimed is:

1. An ultrasound probe head for measuring volume flow in vessels, comprising:
    an ultrasound reflector;
    ultrasound piezo-electric crystals electrically connected by wires to a circuit board electrically connected to a measurement apparatus through an electrical cable;
    a support element, said support element comprising:
        inclined crystal supporting surfaces, disposed on its upper region thereof and symmetrically about a support element vertical axis, and to which said crystals are affixed;
        a bore for passing said electrical cable through said support element; and
        a device for housing said electrical wires in said element;
    said ultrasound probe head further comprising;
        a probe head housing, said housing comprising:
            a compartment for receiving said support element;
            a cable bore for passing said electrical cable received from the support element;
            a recess for receiving a portion of said reflector;
            a wall device for limiting acoustic coupling gel spillage; and
            a wall fixture for retaining the vessel in a stationary position in the probe head.

2. The probe head of claim 1, wherein said ultrasound reflector is attached to said support element by a fastening device.

3. The probe head of claim 1, wherein said housing is made of a resilient material.

4. The probe head housing of claim 3, wherein said resilient material is selected from the group consisting of: silicone, plastics, and rubbers.

5. The probe head of claim 1, wherein said reflector, said ultrasound crystals, and said circuit board are fixedly attached to said support element, and wherein the assembly thereof is sealably coated with a resilient compound.

6. The probe head of claim 1, wherein said probe head housing comprises upper lateral edges formed as inwardly directed flanges adapted to catch the support element upper region.

7. The probe head of claim 1, wherein said probe head housing and said support element are further sealed to constitute one sealed probe head unit, by the application of a resilient compound in the upper region of the housing.

8. The probe head of claim 7, wherein said application of a resilient compound in the upper region of the housing, in combination with said vessel retainer flaps, said reflector, and said gel spill guards, forms a vessel supporting channel with generally planar surfaces, capable of receiving and retaining on its surfaces an acoustic coupling gel.

9. The probe head of claim 5 wherein said resilient compound is selected from the group consisting of: silicone, plastics, and rubbers.

10. The probe head of claim 1, wherein said device for housing said electrical wires in said support element comprises a slit and a wire compartment.

11. The probe head in accordance with claim 8, wherein the resilient vessel retainer flaps are capable of selectively being flexed in order to allow the vessel to be slipped into said generally planar channel, and to releasably secure the vessel in a stationary position in said channel in order to allow flow measurement.

12. The probe head in accordance claim 8, wherein the resilient vessel retainer flaps are capable of selectively being flexed in order to release the vessel from said channel.

13. A probe head for measuring volume flow in vessels, the probe head comprising:
    a housing;
    a recess;
    vessel retainer flaps comprising at least one resilient member that is selectively operable such that the vessel is slipped into and out of the recess, and wherein the support releasably secures the vessel in a stationary position in the recess so as to allow volume flow measurement;
    ultrasound reflector;
    ultrasound piezoelectric crystals that are electrically connected by wires to a circuit board electrically connected to a measurement apparatus through an electrical cable;
    a support element having inclined crystal supporting surfaces disposed on an upper region thereof and symmetrically about the support element's vertical axis and to which the crystals are affixed and a bore for passing the electrical cable through the support element wherein the probe head housing has a compartment receiving the support element, a cable bore passing the electrical cable from the support element, and a recess receiving at least a portion of the ultrasound reflector and wherein the vessel retainer flaps are rigidly attached to the probe housing; and
    gel spill guards for limiting spillage of acoustic coupling gel.

14. The probe head of claim 13, wherein the housing is made of a resilient material.

15. The probe head of claim 14, wherein the resilient material is selected from the group consisting of silicone, plastics, and rubber.

16. The probe head of claim 13, wherein the ultrasound reflector, the ultrasound crystals, and the circuit board are fixedly attached to the support element, and wherein the assembly thereof is sealably coated with a resilient material.

17. The probe head of claim 13, wherein the housing comprises upper lateral edges that are formed as inwardly directed flanges and adapted to catch the support element upper region.

18. The probe head of claim 13, wherein the probe head housing and the assembled support element are further sealed to comprise one sealed probe head unit by a resilient material applied in the upper region of the housing.

19. The probe head of claim 18, wherein the upper region of the housing, in combination with the vessel retainer flaps, the ultrasound reflector, and the gel spill guards, define a vessel supporting channel with generally planar surfaces, which is capable of receiving and retaining on its surfaces an acoustic coupling gel.

20. The probe head of claim 13, wherein the support element bore comprises a slit and a wire compartment.

21. A probe head for measuring volume flow in vessels, the probe head comprising:
    a housing;
    at least one gel spill guard that is capable of receiving and retaining an acoustic coupling gel;
    at least one resilient vessel retainer flap;
    an ultrasound reflector;
    ultrasound piezo-electric crystals that are electrically connected by wires to a circuit board electrically connected to a measurement apparatus through an electrical cable;
    a support element having inclined crystal supporting surfaces disposed on an upper region thereof and symmetrically about the support element's vertical axis and to which the crystals are affixed and a bore for passing the electrical cable through the support element wherein the probe head housing has a compartment receiving the support element, a cable bore passing the electrical cable from the support element, and a recess receiving at least a portion of the ultrasound reflector and wherein the vessel retainer flaps are rigidly attached to the probe housing; and
    resilient compound joining the housing, the at least one gel spill guard, and the at least one resilient vessel retainer flap so as to define a vessel supporting channel wherein the resilient vessel retainer flap is capable of releasably securing a vessel in a stationary position in the vessel supporting channel in a manner so as to allow volume flow measurement in the vessel.

22. The probe head of claim 21, wherein the resilient material comprises at least one of silicone, plastics, and rubbers.

23. The probe head of claim 21, wherein the housing comprises resilient material.

* * * * *